United States Patent [19]

Regnat et al.

[11] Patent Number: 5,719,309
[45] Date of Patent: Feb. 17, 1998

[54] PROCESS FOR PREPARING 4-BROMOMETHYL-3-METHOXY-BENZOIC ESTERS

[75] Inventors: Dieter Regnat, Eppstein; Hans-Jerg Kleiner, Kronberg, both of Germany

[73] Assignee: Hoechst Aktiengesellschaft, Germany

[21] Appl. No.: 702,981

[22] Filed: Aug. 26, 1996

[30] Foreign Application Priority Data

Aug. 24, 1995 [DE] Germany .................. 195 31 164.7

[51] Int. Cl.⁶ .................................................. C07C 69/76
[52] U.S. Cl. .................................................. 560/65
[58] Field of Search ..................................... 560/65

[56] References Cited

FOREIGN PATENT DOCUMENTS 0595150  5/1994  European Pat. Off. .

OTHER PUBLICATIONS

Angew. Chemie Int. Ed., Bd. 19, Nr. 6, 1980, pp. 464–465; W. Offermann; F. Vögtle: "Brominations with N–Bromosuccinimide: Solvent and Selectivity".

Chem. Ber., Bd. 114, 1981, pp. 1048–1064, K. Böckmann, F. Vögtle: "Intraanular phenyl–substituierte Phane—Synthese und dynamische Stereochemie".

J. Med. Chem., Bd. 33, 1990, pp. 1771–1781, F.J. Brown et al.: "Evolution of a Series of Peptidoleukotriene Antagonists".

*Primary Examiner*—Paul J. Killos
*Attorney, Agent, or Firm*—Connolly and Hutz

[57] ABSTRACT

A process for preparing 4-bromomethyl-3-methoxybenzoic esters of the formula

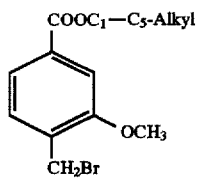

entails the corresponding 4-methyl-3-methoxybenzoic esters being reacted in chlorobenzene or an ester as solvent with N-bromosuccinimide with exposure to light of wavelength $10^{-5}$ to $10^{-8}$ m at $-10°$ to $120°$ C.

3 Claims, No Drawings

PROCESS FOR PREPARING 4-BROMOMETHYL-3-METHOXY-BENZOIC ESTERS

4-Bromomethyl-3-methoxybenzoic ester, in particular the methyl ester, is an important intermediate, for example for the preparation of peptidoleukotriene antagonists (J. Med. Chem. 33 (1990) 1771, U.S. Pat. No. 4, 894,386, EP 337 767, EP 337 766, EP 290 145, JP 6 206 465), of antiinflammatory pharmaceuticals (U.S. Pat. No. 5,280,039) and testosterone 5α-reductase inhibitors (EP 519 353).

Methyl 4-bromomethyl-3-methoxybenzoate can be prepared by side-chain bromination of methyl 4-methyl-3-methoxybenzoate, either with bromine or with N-bromosuccinimide. The required product is obtained in a yield of 64 to 95% (J. Med. Chem. 33 (1990) 1771; J. Med. Chem. 31 (1988) 692; J. Am. Chem. Soc. 101 (1979) 1857). Carbon tetrachloride is used as solvent in all these cases, but is a marked cytotoxin with the main effect on the liver and kidney. Industrial use of this solvent is therefore prohibited or greatly restricted. The object therefore is to develop a process for brominating 4-methyl-3-methoxybenzoic esters which does not use such a toxic solvent. This object has been achieved by a photochemical reaction with N-bromosuccinimide in chlorobenzene or certain carboxylic esters as described hereinafter. In view of the prior art mentioned, it was surprising that the target product is obtained in this novel process, which dispenses with the problematic solvent carbon tetrachloride, in yields which are as high as in the prior art.

The invention relates to a process for preparing 4-bromomethyl-3-methoxybenzoic esters of the formula

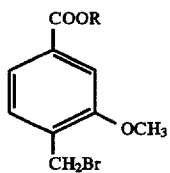

where R is $C_1$–$C_5$-alkyl, which comprises reacting 4-methyl-3-methoxybenzoic esters of the formula

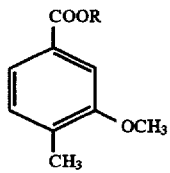

in which R has the abovementioned meaning, in chlorobenzene or an ester of the formula

in which $R_2$ is hydrogen or $C_1$–$C_3$-alkyl and $R_3$ is $C_1$–$C_4$-alkyl, with N-bromosuccinimide with exposure to light of wavelength $10^{-5}$ to $10^{-8}$ m at $-10°$ to $120°$ C.

It is known from the course of the reaction in halogenations of organic compounds that a halogenation in the side chain of an aromatic compound is normally carried out at rather high temperatures (boiling point) in the presence of light (sunlight), whereas the halogenation of the nucleus takes place at low temperatures with use of a catalyst.

With this background, it must be regarded as surprising that the halogenation according to the invention with exposure to light at comparatively low to very low temperatures results in negligible halogenation of the aromatic nucleus and, on the contrary, results in halogenation of the methyl group with high selectivity.

In general, the amount of solvent used is of no great importance. However, its quantity should be sufficient. It generally suffices to use methyl 4-methyl-3-methoxybenzoate and the solvent in a ratio by weight of 1:(3 to 40), in particular 1:(4 to 20), preferably 1:(5 to 15).

The solvent used is chlorobenzene or an ester of an aliphatic carboxylic acid with 1 to 4 carbon atoms and of an aliphatic alcohol with 1 to 4 carbon atoms or mixtures.

Examples of suitable solvents are chlorobenzene, methyl formate, ethyl formate, methyl acetate, ethyl acetate, propyl acetate, butyl acetate, methyl propionate, ethyl propionate, propyl propionate, butyl propionate, methyl butyrate, ethyl butyrate, propyl butyrate and butyl butyrate. Mixtures of these solvents can also be used. Very suitable solvents are chlorobenzene and ethyl acetate.

4-Methyl-3-methoxybenzoic ester and N-bromosuccinimide are normally used in the molar ratio of 1:(0.9 to 1.5). In many cases it suffices to use methyl 4-methyl-3-methoxybenzoate and N-bromosuccinimide in the molar ratio of 1:(0.95 to 1.3), preferably 1:(1.0 to 1.2).

During the halogenation, succinimide is produced from N-bromosuccinimide as reaction product. The succinimide can be removed by filtration, where appropriate after cooling the solution containing the reaction mixture. Another possibility is to remove the succinimide which has formed by extraction with water. Normally used for this purpose are 10 to 100% by weight of water based on the reaction mixture.

A particularly simple and, at the same time, effective method for removing succinimide is to remove the succinimide which has formed from the reaction mixture by filtration in a first step and by extraction with water in a second step. In this case, comparatively little water is used and, correspondingly, little waste water is obtained.

The process according to the invention is carried out with exposure to light. A possible light source is a conventional UV emitter, for example a sun lamp, a doped or undoped mercury vapor lamp or low-pressure mercury vapor lamp. These light sources have a spectrum from $10^{-5}$ to $10^{-8}$, in particular $10^6$ to $2 \times 10^{-7}$ m. This also comprises the light fractions, in particular UV fractions, necessary for the reaction.

If required, the reaction can also be carried out in the presence of a free-radical former. This is because it has emerged that addition of a free-radical former (free-radical initiator) may in some cases have a beneficial effect in addition to the exposure to light. Suitable free-radical formers are the free-radical formers customary for free-radical halogenation, for example organic peroxides, organic percarboxylic acids, organic hydroperoxides or organic azo compounds.

Examples of suitable free-radical formers are benzoyl peroxide, benzoyl perhexadecanoate and azobisisobutyronitrile.

Unreacted free-radical formers can be removed, for example, by washing with an aqueous $Na_2SO_3$ solution.

The free-radical formers are used in customary amounts. As a rule, a sufficient amount is from 0.1 to 5, in particular 0.5 to 2,% by weight based on 4-methyl-3-methoxybenzoic ester.

As already mentioned at the outset, the bromination is carried out at $-10°$ to $120°$ C. In many cases, it has proven sufficient to allow the bromination to take place from $-5$ to 100, in particular $0°$ to $80°$ C.

It may be desirable, for any further processing of the reaction mixture resulting after the bromination, to replace the solvent originally used in the bromination stage by another solvent. This is particularly necessary when the original solvent is not inert under the conditions of the further processing, for example on exposure to basic substances. In this case, another solvent which has a higher boiling point than the originally used solvent is added to the reaction mixture after the halogenation, and subsequently the originally used solvent is distilled out, completely or partially depending on the requirements and needs.

Suitable as the other solvent are aromatic hydrocarbons, for example toluene, o-xylene, m-xylene, p-xylene, mixtures of these xylenes, ethylbenzene and/or mesitylene, and higher-boiling aliphatic hydrocarbons, for example petroleum ether with a boiling point >100° C., decalin, mineral spirits and/or isooctane. If the solvent replacement is to be carried out under particularly mild conditions, the originally used solvent can be distilled out as azeotrope and/or under reduced pressure.

If it is intended to isolate the 4-bromomethyl-3-methoxybenzoic ester as pure product, succinimide which is formed where appropriate is removed as described previously by filtration and/or extraction with water, the reaction mixture is dried, and the desiccant is filtered off. Subsequently, the originally used solvent is removed under reduced pressure. A crystalline product is obtained and is, where appropriate, purified by recrystallization. The purity of the resulting crude product is generally sufficient for further use.

EXAMPLE 1

18.02 g (0.1 mol) of methyl 3-methoxy-4-methylbenzoate and 18.68 g (0.105 mol) of N-bromosuccinimide are introduced into 150 ml of ethyl acetate and illuminated with a UV immersion lamp at 0° to 5° C. for 4 hours. The mixture is extracted with 150 ml of water, dried with sodium sulfate, filtered and concentrated in vacuo. 25.9 g of colorless crystals are obtained, and after recrystallization from n-heptane/ethyl acetate in the ratio 2:1 24.6 g (95%) of colorless crystals of melting point 90° C.

EXAMPLE 2

18.02 g (0.1 mol) of methyl 3-methoxy-4-methylbenzoate and 18.68 g (0.105 mol) of N-bromosuccinimide are introduced into 150 ml of chlorobenzene and illuminated with a UV immersion lamp at 0° to 5° C. for 4 hours. The mixture is extracted with 150 ml of water, dried with sodium sulfate, filtered and concentrated in vacuo. 25.9 g of colorless crystals are obtained, and after recrystallization from n-heptane/ethyl acetate in the ratio 2:1 23.3 g (90%) of colorless crystals of melting point 90° C.

We claim:

1. A process for preparing 4-bromomethyl-3-methoxybenzoic esters of the formula

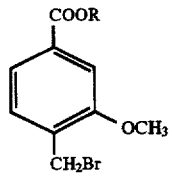

where R is $C_1$–$C_5$-alkyl, which comprises reacting 4-methyl-3-methoxybenzoic esters of the formula

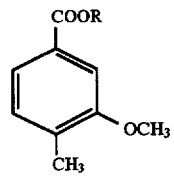

in which R has the abovementioned meaning, in chlorobenzene or an ester of the formula

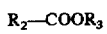

in which $R_2$ is hydrogen or $C_1$–$C_3$-alkyl and $R_3$ is $C_1$–$C_4$-alkyl, with N-bromosuccinimide with exposure to light of wavelength $10^{-5}$ to $10^{-8}$ m at $-10°$ to $120°$ C.

2. The process as claimed in claim 1, wherein the reaction is carried out in the presence of a free-radical former.

3. The process as claimed in claim 1, wherein the reaction is carried out in the presence of chlorobenzene, methyl formate, ethyl formate, methyl acetate, ethyl acetate or n-propyl acetate.

* * * * *